(12) United States Patent
Liu

(10) Patent No.: US 7,832,914 B2
(45) Date of Patent: Nov. 16, 2010

(54) AUXILIARY POSITIONING DEVICE FOR ULTRASONIC APPARATUS

(75) Inventor: Sen-Yung Liu, Changhua (TW)

(73) Assignee: Changhua Christian Hospital, Changhua (TW)

( * ) Notice: Subject to any disclaimer, the term of this patent is extended or adjusted under 35 U.S.C. 154(b) by 0 days.

(21) Appl. No.: 12/704,561

(22) Filed: Feb. 12, 2010

(65) Prior Publication Data

US 2010/0142210 A1    Jun. 10, 2010

Related U.S. Application Data

(62) Division of application No. 11/549,119, filed on Oct. 13, 2006.

(51) Int. Cl.
*A61B 1/06* (2006.01)
(52) U.S. Cl. .................. 362/572; 606/437; 606/459; 606/461
(58) Field of Classification Search .......... 362/319, 362/320, 570, 572, 574, 581, 396, 551, 553, 362/261, 555, 558; 606/130; 600/437, 459, 600/461
See application file for complete search history.

(56) References Cited

U.S. PATENT DOCUMENTS

| | | | | |
|---|---|---|---|---|
| 4,123,135 A | * | 10/1978 | Rabedeau | 359/218.1 |
| 5,163,752 A | * | 11/1992 | Copeland et al. | 362/396 |
| 5,255,167 A | * | 10/1993 | Toussaint et al. | 362/103 |
| 5,311,348 A | * | 5/1994 | Yamakawa | 359/216.1 |
| 5,461,790 A | * | 10/1995 | Olstowski | 30/391 |
| 5,638,214 A | * | 6/1997 | Doric | 359/654 |
| 5,823,657 A | * | 10/1998 | Price et al. | 362/191 |
| 5,948,172 A | * | 9/1999 | Neiheisel | 134/1 |
| 6,322,958 B1 | * | 11/2001 | Hayashi | 430/495.1 |

* cited by examiner

*Primary Examiner*—Jong-Suk (James) Lee
*Assistant Examiner*—Julie A Shallenberger

(57) ABSTRACT

An auxiliary positioning device for an ultrasonic apparatus is disclosed herein, which is installed on an ultrasonic probe. The auxiliary positioning device includes a fixing member, an adjusting member being flexible and coupled with the fixing member at one end thereof, a parallel light source coupled with the other end of the adjusting member and having a projection hole for passing a parallel light beam emitted from the parallel light source, and a cylindrical lens mounted on one end of the parallel light source in front of the projection hole, whereby the parallel light beam becomes a fanned light beam after it passes through the cylindrical lens. The auxiliary positioning device of the present invention can provide a high precise positioning for diagnosis and treatment.

10 Claims, 9 Drawing Sheets

AUXILIARY POSITIONING DEVICE FOR ULTRASONIC APPARATUS

CROSS-REFERENCES TO RELATED APPLICATIONS

This is a division of U.S. application Ser. No. 11/549,119, filed Oct. 13, 2006, which is incorporated herewith by reference.

BACKGROUND OF THE INVENTION

1. Field of the Invention

The present invention relates to an auxiliary positioning device, and in particular to an auxiliary positioning device for an ultrasonic apparatus.

2. The Prior Arts

In general, an ultrasonic apparatus is often used to scan and inspect a patient's inner organ. The ultrasonic apparatus can receive an echo to conclude the position of the organ and visualize an image of the organ tissue on a screen. Accordingly, the patient can be further diagnosed and treated based on the displayed images. During the operation of the ultrasonic apparatus, it is only requested to clearly display the image if the ultrasonic apparatus is merely used to inspect the physiological structure. However, if a further diagnosis and treatment such as a sample collection or an injection is needed, an accurate position must be determined. Generally, a three dimensional image can be obtained by scanning an interior of the human body. If a certain area in the body is intended to be sample-collected or injected, an auxiliary positioning device is often needed to help the positioning unless it is performed by a skilled operator. Otherwise, it is difficult to insert a needle into a correct position, thereby resulting in the increase in the possibility of failure and in the times of the needle insertion that will increase the mental pressure and physical pains to the patient.

Please refer to FIG. 1, which is a schematic view showing an injection into a body surface of a patient B by means of the guidance of an ultrasonic probe according to a prior art. Before the injection is performed, an ultrasonic probe P is used to scan the body surface of the patient B until a target position is detected. When the ultrasonic probe P reaches the target position, a needle of a syringe S can be inserted into the body of the patient B. At this time, in order to ensure the position to be injected is correct, the needle of the syringe S and the position to be injected must be fully detected by the ultrasonic probe P and completely displayed on a screen. However, it is difficult for a medical operator to perform. As described above, the image obtained by scanning the interior of the body of the patient is a three dimensional image. Even though a correct position is located, if the syringe S and the area detected by the ultrasonic probe P are not in the same plane but displayed together on the screen in a two dimensional image, the operator still has to insert the needle of the syringe S for several times to reach the correct position based on his/her experiences and feelings. As a result, it will make the patient feel uncomfortable mentally and physically. On the other hand, in order to make the image display on the screen more clearly and brightly, the light is often turned down during performing the diagnosis and treatment on patients. However, under such circumstances, it becomes more difficult to find the correct position for insertion by the needle of the syringe S.

SUMMARY OF THE INVENTION

A primary objective of the present invention is to provide an auxiliary positioning device for an ultrasonic apparatus, which can generate a fanned light beam by refracting a parallel light beam through a cylindrical lens. The fanned light beam projects a projection line for accurately locating a position on a body surface of a patient to be diagnosed and treated, thereby solving the problem that a conventional ultrasonic probe is unable to locate an accurate position to be diagnosed and treated. Besides, by the means of the projection line, a position to be treated can be accurately located even in a dark condition. Accordingly, a syringe can be adjusted to be in alignment with the ultrasonic probe through the projection line, so that a needle of the syringe can be inserted into the correct position on the body surface of the patient for treatment.

To achieve the above-mentioned objectives, an auxiliary positioning device for an ultrasonic apparatus in accordance with the present invention, which is installed on an ultrasonic probe, includes a fixing member, an adjusting member being flexible and coupled with the fixing member at one end thereof, a parallel light source coupled with the other end of the adjusting member and having a projection hole for passing a parallel light beam emitted from the parallel light source, and a cylindrical lens mounted on one end of the parallel light source in front of the projection hole, whereby the parallel light beam becomes a fanned light beam after it passes through the cylindrical lens.

According to the present invention, the parallel light source may be a laser light source or other light sources. The fixing member may be a fixing clamp or a clamp that is sleeved on the ultrasonic probe and fastened thereto with screws. There is no limitation to the structure of the fixing member as long as it can fix the auxiliary positioning device to the ultrasonic probe. The adjusting member is used to adjust a desired angle and a range of the projection light emitted from the parallel light source. The adjusting member may be, but not limited to, a flexible member in accordance with the present invention. Any flexible or bendable adjusting member such as a multiple rod linkage with ball pivot mechanisms is applicable. The cylindrical lens may be a circular, biconvex, biconcave, plano-convex, or plano-concave cylindrical lens.

According to the present invention, the parallel light beam enters into the cylindrical lens and is refracted to a fanned light beam, which can project a projection line on a surface of an object. By means of the projection line, a needle of a syringe can be in alignment with the ultrasonic probe even in a dark condition, so that the needle can be inserted into a correct position to be diagnosed and treated. Accordingly, this can prevent the patient from being inserted many times by a needle, which will cause uncomfortable feeling.

The advantages and spirit of the present invention can be more clearly understood from the following detailed description, taken in conjunction with the accompanying drawings.

DETAILED DESCRIPTION OF THE PREFERRED EMBODIMENT

Figure 1:
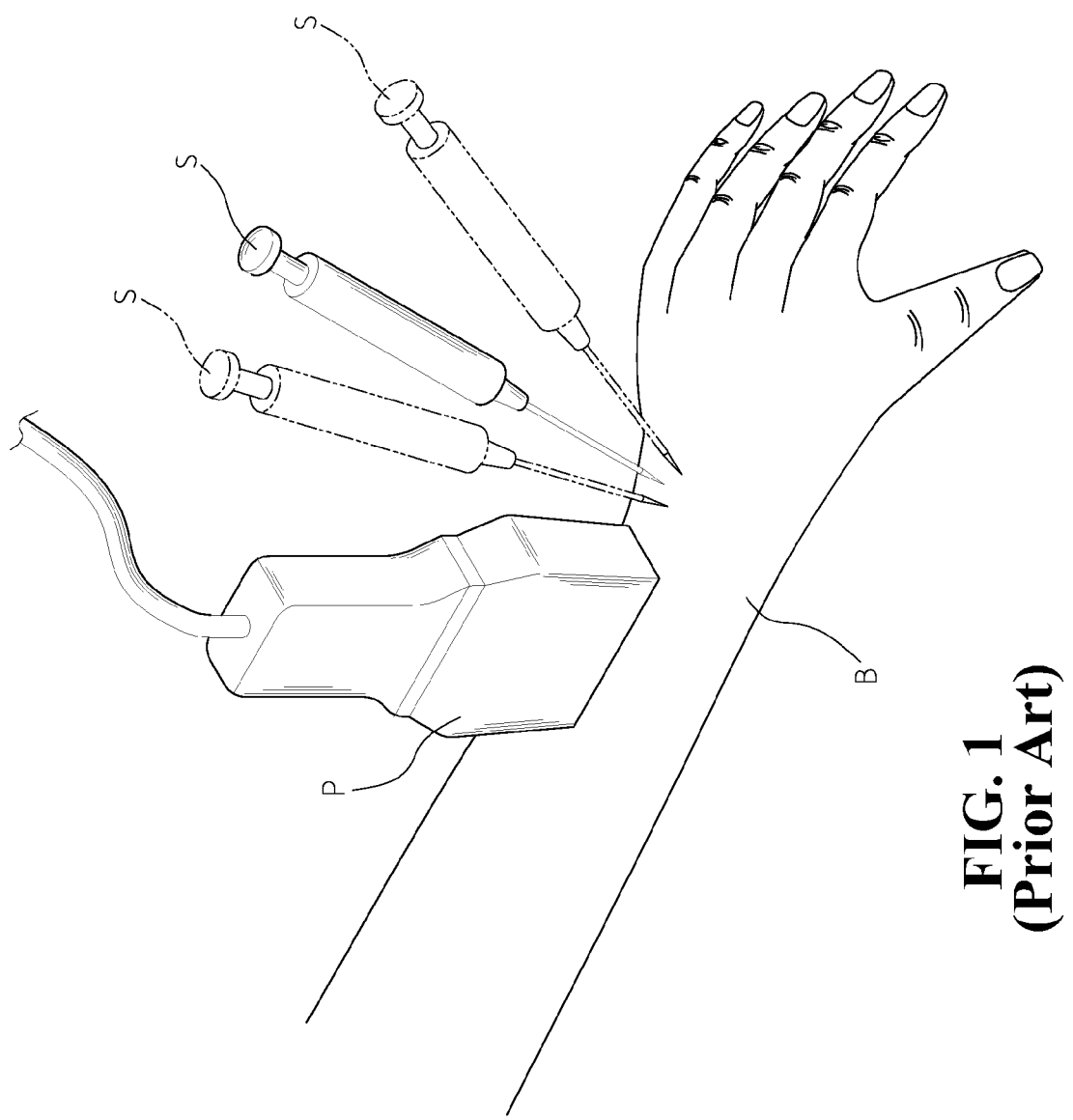
FIG. 1 is a schematic view showing an injection into a body surface of a patient by means of the guidance of an ultrasonic probe according to a prior art.
Figure 2:
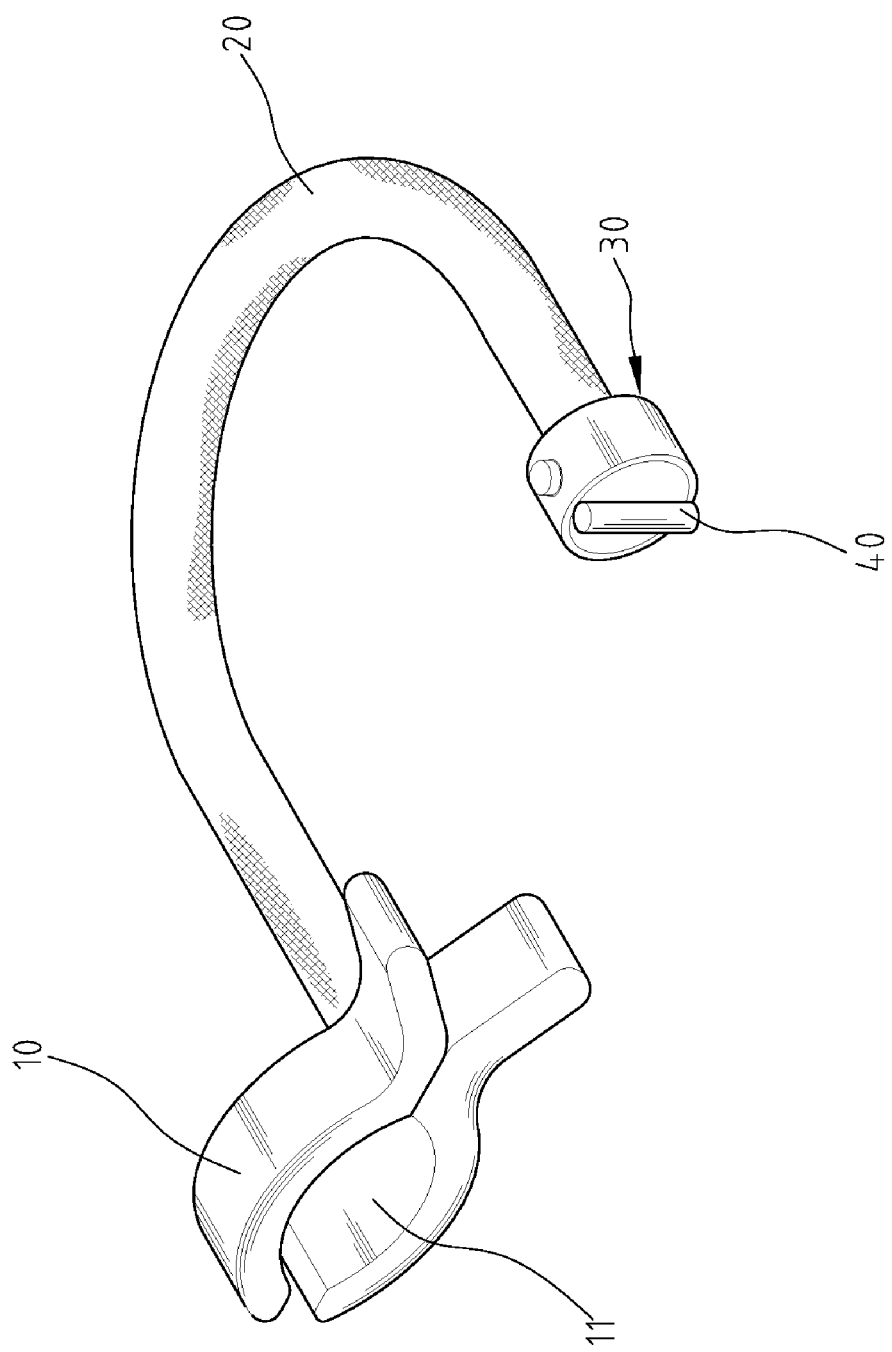
FIG. 2 is a perspective view of an auxiliary position device for an ultrasonic apparatus in accordance with an embodiment of the present invention.
Figure 4:
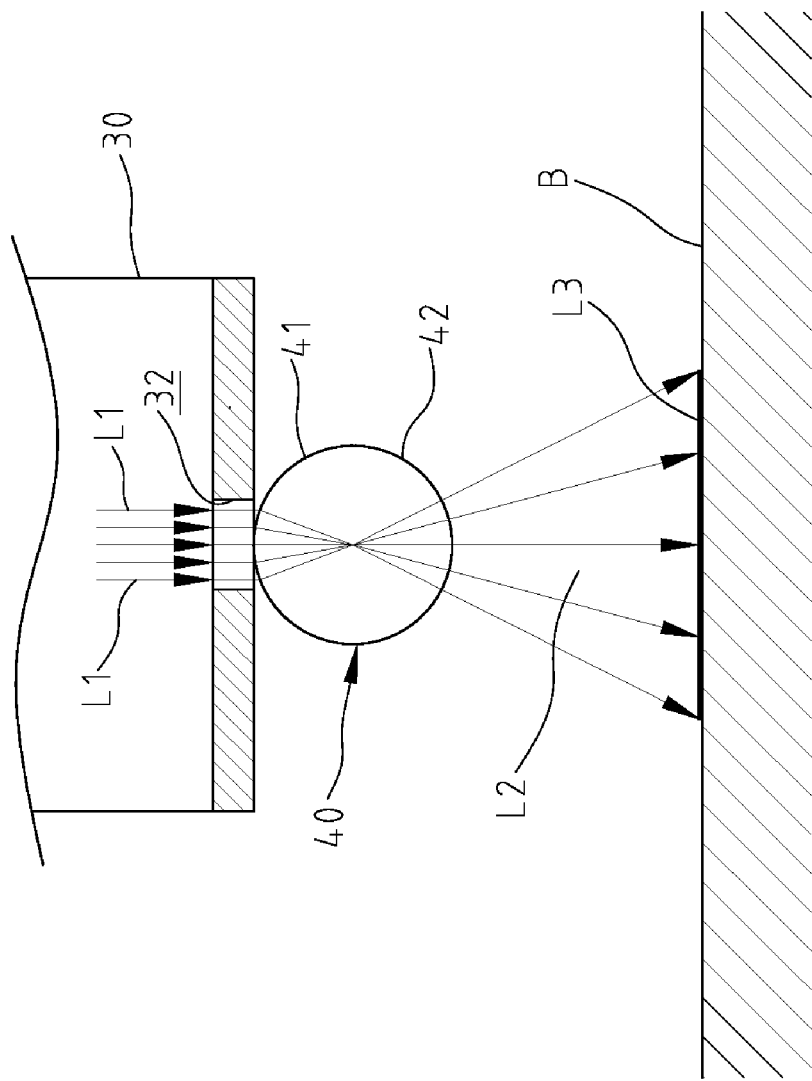
FIG. 4 is a schematic view showing a path of a parallel light beam penetrating through the cylindrical lens.
Figure 5C:
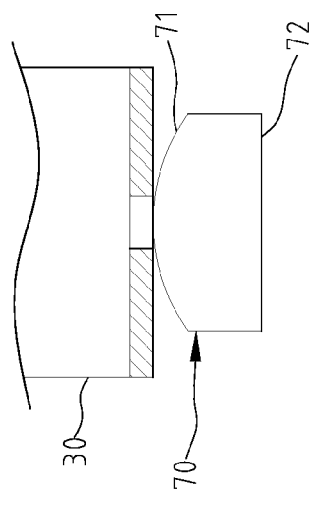
FIGS. 5A-5E are schematic views showing different types of cylindrical lenses in accordance with the present invention.
Figure 5B:
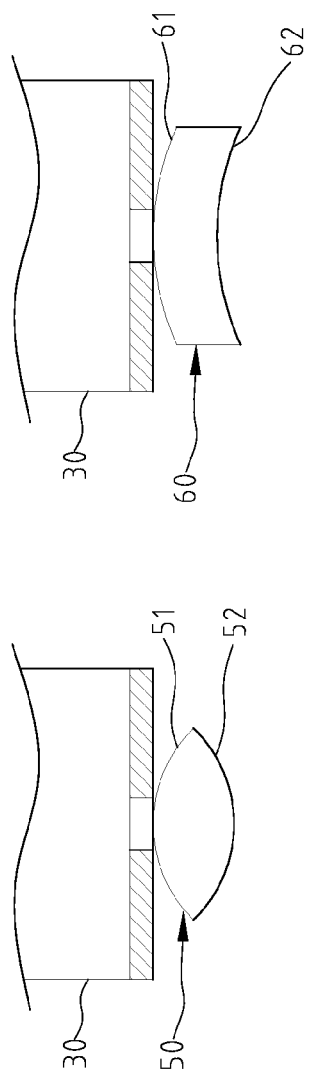
Figure 5A:
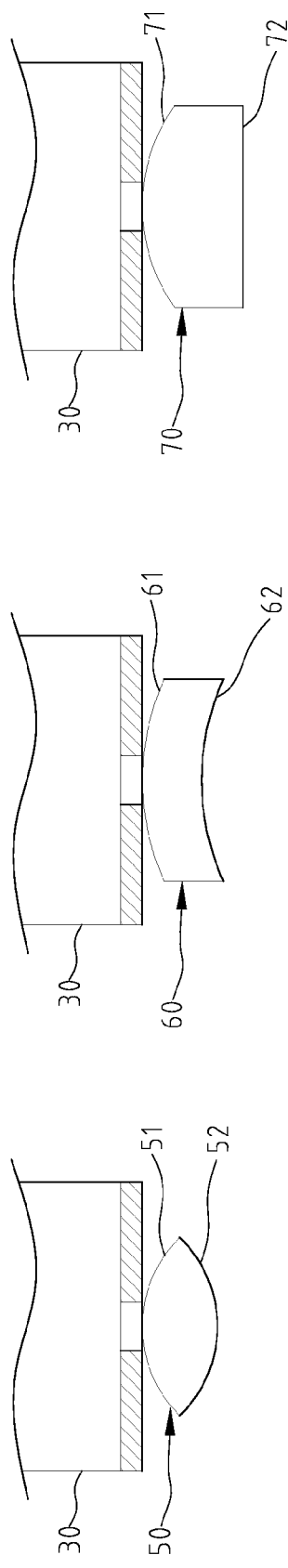
Figure 5E:
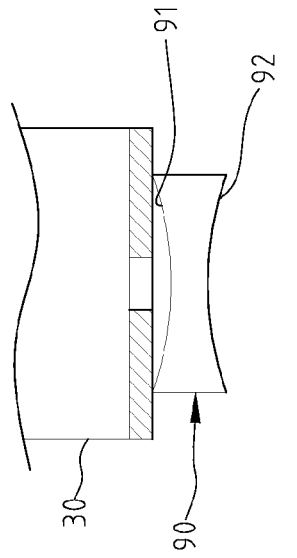
Figure 5D:
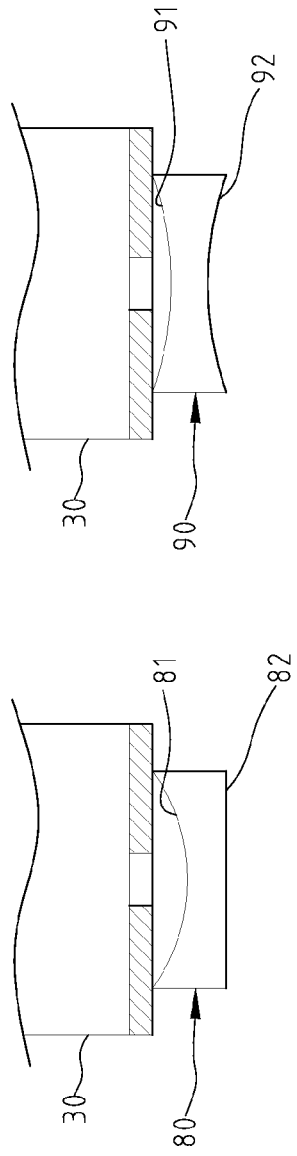

Referring to FIGS. 2 and 4, an auxiliary positioning device for an ultrasonic apparatus in accordance with an embodiment of the present invention comprises a fixing member 10, an adjusting member 20, a parallel light source 30 and a cylindrical lens 40. The fixing member 10 is coupled with one end of the adjusting member 20 and the parallel light source 30 is coupled with the other end of the adjusting member 20. The cylindrical lens 40 is mounted on an end surface of the parallel light source 30, whereby a fanned light beam L2 is projected out of the cylindrical lens 40 when a parallel light beam L1 emitted from the parallel light source 30 passes through the cylindrical lens 40. The fanned light beam L2 is projected onto a surface of a patient B to form a projection line L3 for auxiliary positioning for an ultrasonic apparatus.

The fixing member 10 is, but not limited to, a fixing clamp in this embodiment. The fixing member 10 has a jaw 11 configured to stably hold an ultrasonic probe P (see FIGS. 6A and 6B). Moreover, the fixing member 10 may have a frame (not shown) configured with an outer shape of the ultrasonic probe P and sleeved and fixed thereto with screws.

The adjusting member 20 is used to adjust a desired angle and a range of the projection light emitted from the parallel light source 30. The adjusting member 20 may be, but not limited to, a flexible member in this embodiment. Any flexible or bendable adjusting member 20 such as a multiple rod linkage with ball pivot mechanisms is applicable. There is no limitation to the bending angle of the adjusting member 20 and it can be adjusted according to the length and the size of the ultrasonic probe P.

The parallel light source 30 is, but not limited to, a laser light source in this embodiment. Any light sources that emit a parallel light beam may be used in the present invention. But a diameter of the light beam of the parallel light source 30 cannot be too large; otherwise it will be difficult to align with a baseline on the ultrasonic probe P accurately.

Figure 3A:
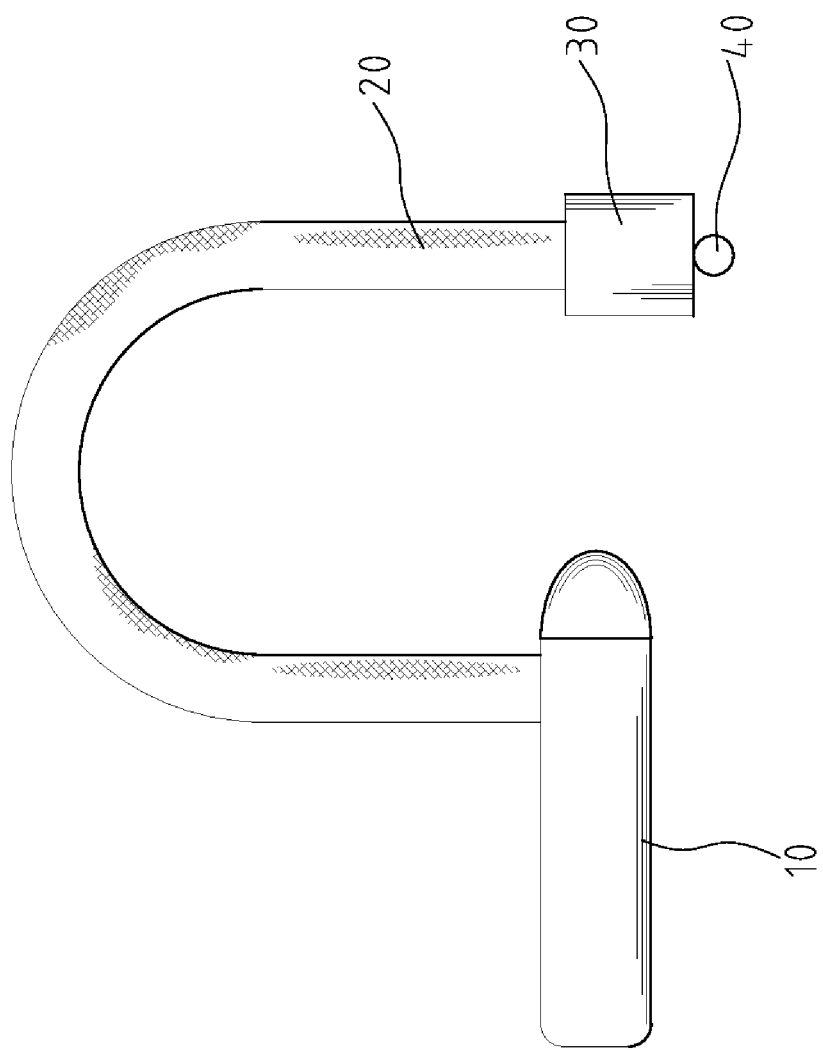
FIG. 3A is a side view of FIG. 2.
Figure 3B:
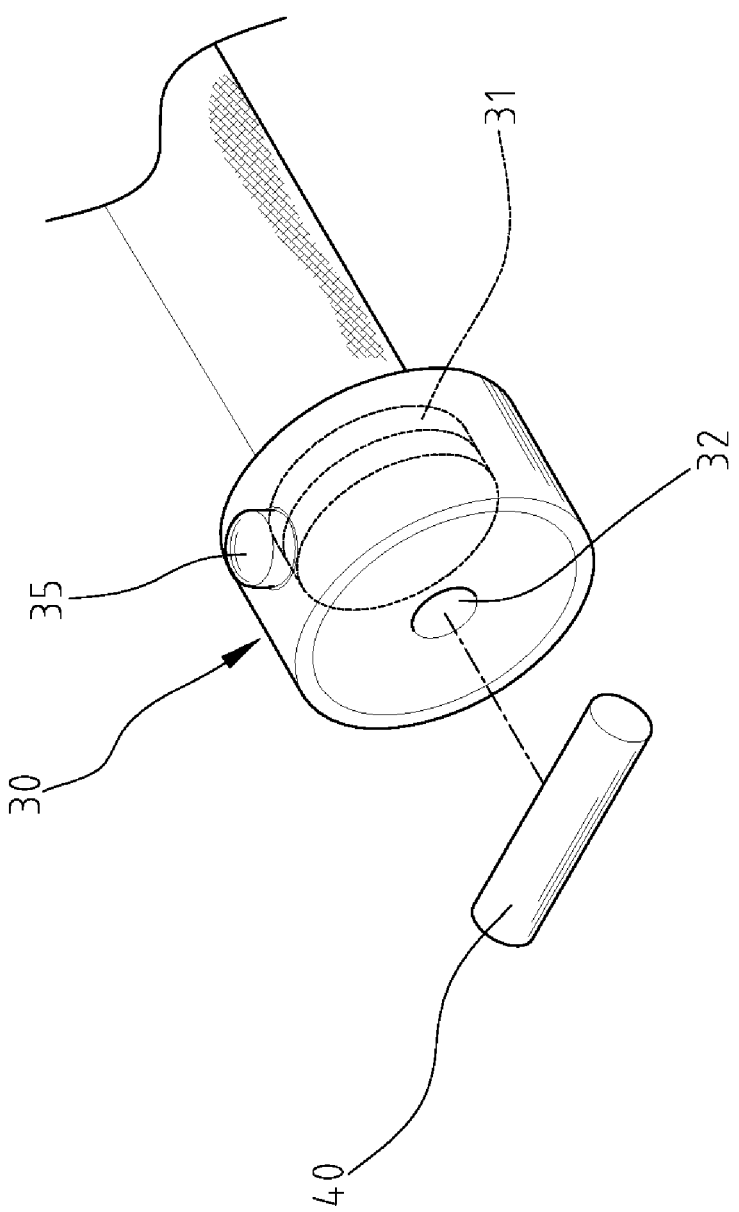
FIG. 3B is an enlarged view showing a parallel light source and a cylindrical lens in accordance with the present invention.
Figure 7:
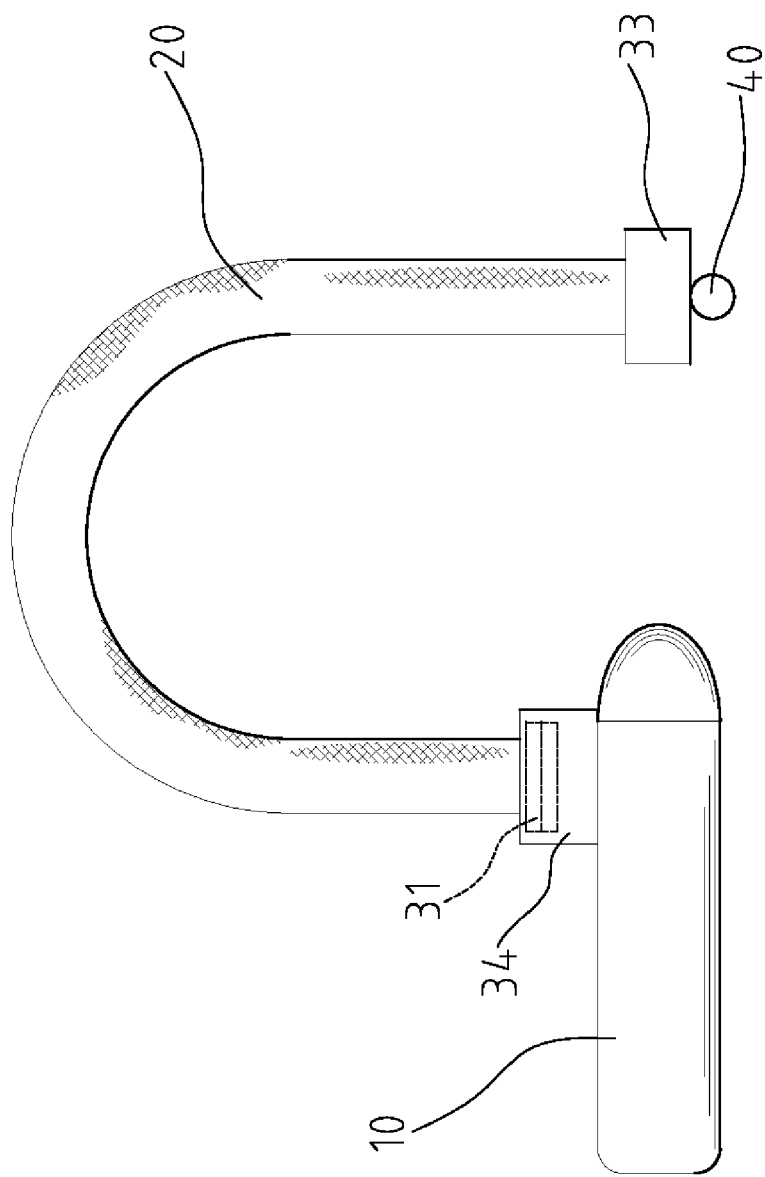
FIG. 7 is a schematic view of an auxiliary positioning device for an ultrasonic apparatus in accordance with another embodiment of the present invention.

Referring to FIGS. 3A and 3B, the parallel light source 30 has a projection hole 32 defined on one end surface thereof for passing the parallel light bean. A diameter of the projection hole 32 determines the diameter of the projection light emitted from the parallel light source 30. The parallel light source 30 comprises a battery 31 to provide power supply and a switch 35 to turn on/off the power supply. In this embodiment, the switch 35 is located on the parallel light source 30, but it may be located on the adjusting member 20 or the fixing member 10 as well. On the other hand, the battery 31 in the present invention is a button battery, but it can also be a lithium battery or alkaline battery. Accordingly, the parallel light source 30 can be constructed to receive different types of batteries. The battery 31 can be placed in a battery pack 34 disposed between the fixing member 10 and the adjusting member 20, whereby the projection head 33 of the parallel light source 30 is lighter (see FIG. 7). At this time, the switch 35 is provided on the battery pack 34. Besides, the cylindrical lens 40 is set in a direction parallel to the fixing member 10.

Referring to FIG. 4, a parallel light beam L1 emitted from the parallel light source 30 through the projection hole 32 enters into a lens surface 41 of the cylindrical lens 40, which is closest to the parallel light source 30, and goes out of a lens surface 42 of the cylindrical lens 40, which is farthest from the parallel light source 30. The parallel light beam L1 becomes a fanned light beam L2 caused by refraction of the light from the cylindrical lens 40. The fanned light beam L2 projects on a surface of a patient B to form a projection line L3, which can be precisely applied to locate a correct position for injection.

The cylindrical lens 40 is a circular cylindrical lens as shown in FIG. 4. Referring to FIGS. 5A-5E, the cylindrical lens 40 according to the present invention may be a biconvex cylindrical lens 50, a convex-concave cylindrical lens 60, a plano-convex cylindrical lens 70, a plano-concave cylindrical lens 80, a biconcave cylindrical lens 90, or combinations thereof. Accordingly, the parallel light beam L1 can enter into a lens surface 51, 61, 71, 81 or 91 of the cylindrical lens, which is closest to the parallel light source 30, and goes out of a lens surface 52, 62, 72, 82 or 92 of the cylindrical lens, which is farthest from the parallel light source 30, respectively. On the other hand, a length of the cylindrical lens 40 should be greater than the diameter of the projection hole 32, so that the parallel light beam L1 can be projected completely.

Figure 6A:
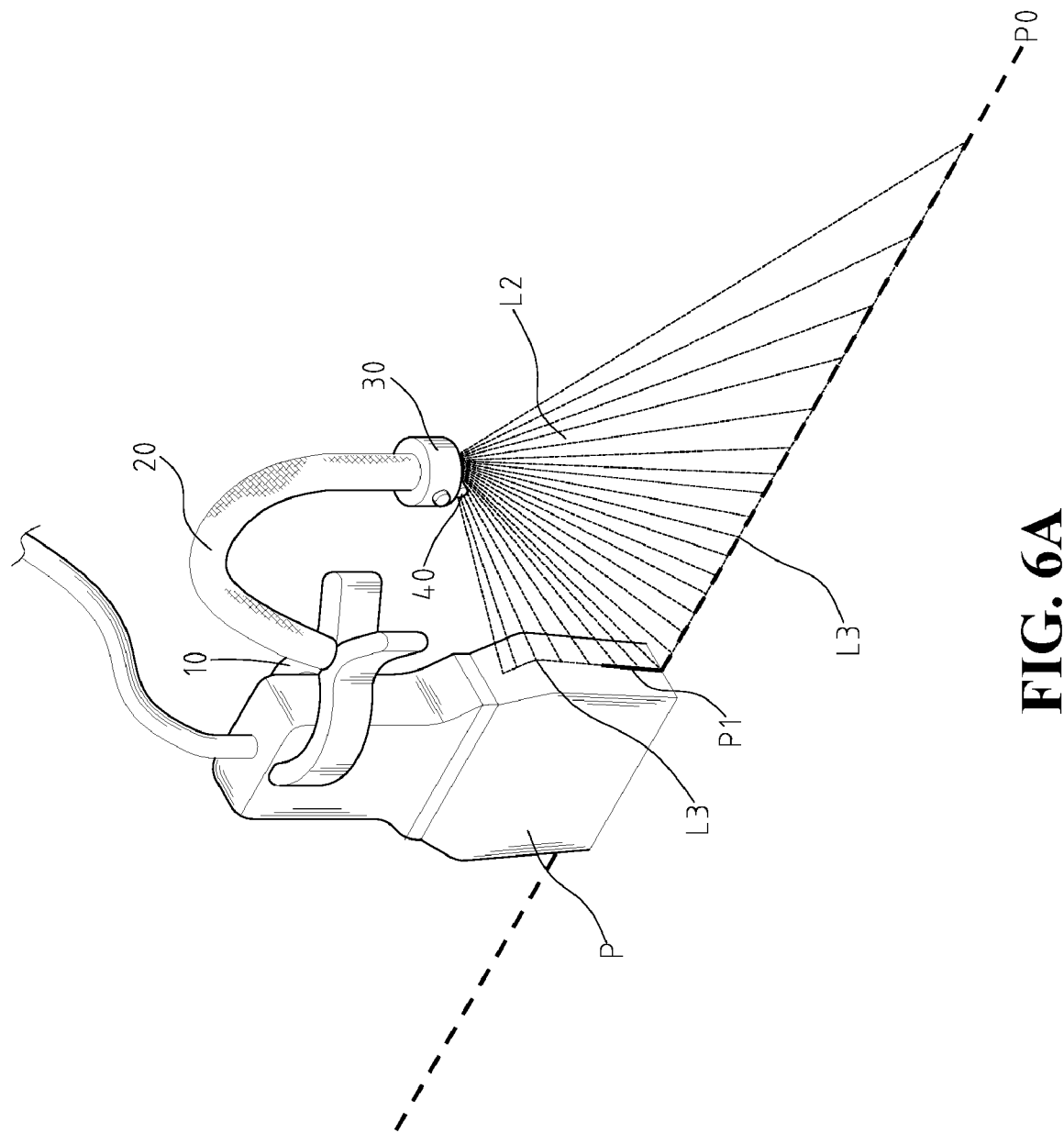
FIG. 6A is a schematic view showing a correction of the auxiliary positioning device installed on an ultrasonic probe in accordance with the present invention.
Figure 6B:
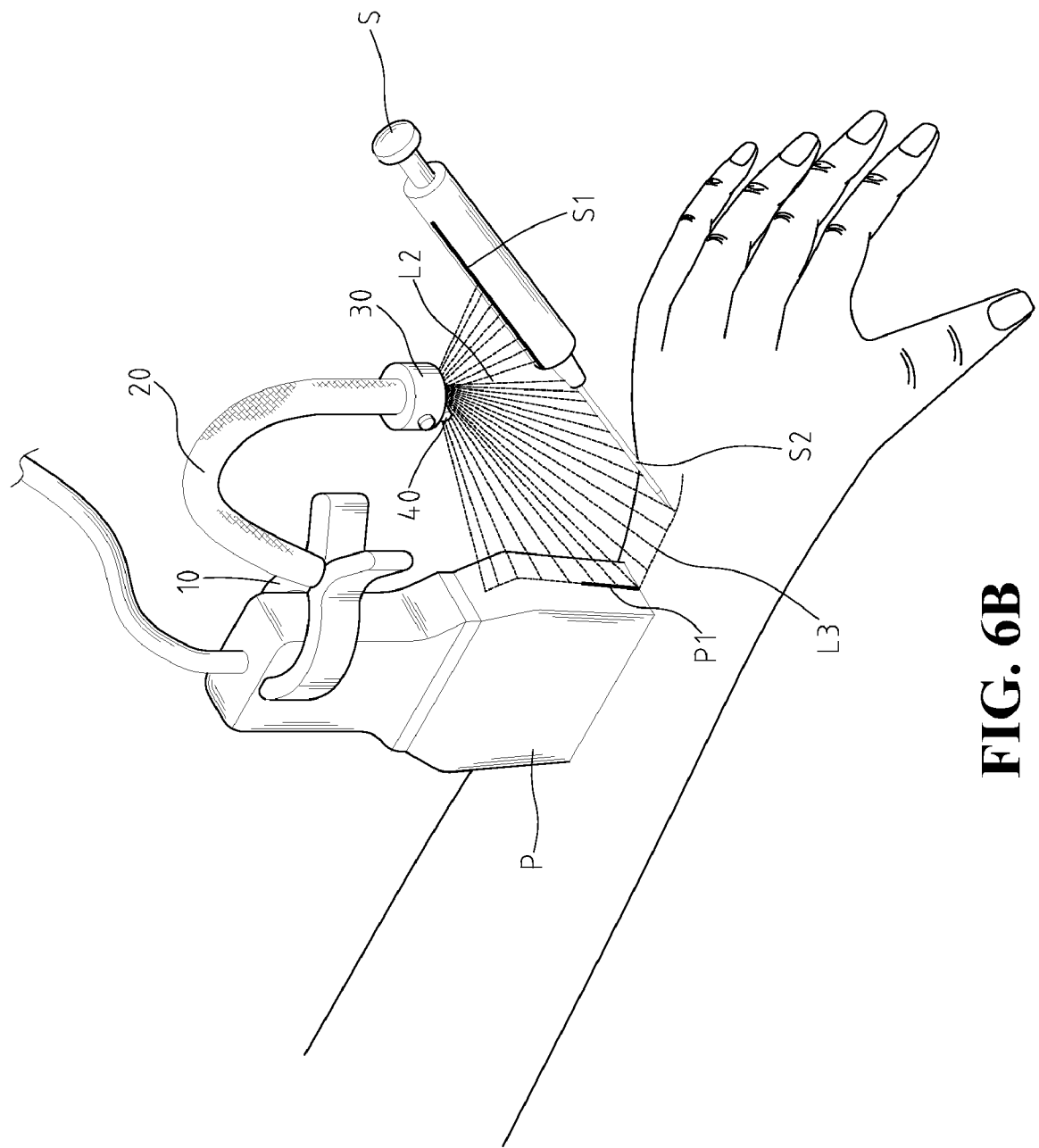
FIG. 6B is a schematic view showing that FIG. 6A is in a use state.

Referring to FIGS. 6A and 6B, a surface of the ultrasonic probe P is marked with a baseline P1 that is aligned with a scanning sectional plane of the ultrasonic probe P. The auxiliary positioning device for an ultrasonic apparatus in accordance with the present invention is fixed on the ultrasonic probe P in advance, and the adjusting member 20 is bent downwardly. Then the ultrasonic probe P is placed on and aligned with a correction line P0 defined on a surface of an object, so that the scanning sectional plane and the baseline P1 on the ultrasonic probe P are aligned with the correction line P0. The adjusting member 20 is adjusted to make the projection line L3 overlap and align with the baseline P1; thereby the fanned light beam L2 emitted from the parallel light source 30, the projection line L3, the scanning sectional plane, and the baseline P1 are all located on the same plane vertical to the object surface. During injection, a syringe S having a surface marked with a baseline S1 is provided. After the ultrasonic probe P scans a position to be injected, a needle S2 of the syringe S can be inserted into the accurate position by the alignment of the baseline S1 of the syringe S with the projection line L3. Since the needle S2 and the scanning sectional plane are in the same plane, the needle S2 together with the injection position can be detected by the ultrasonic probe P and displayed on a screen. Accordingly, the needle S2 can be accurately and rapidly inserted into the position to be injected or extracted, so as to perform the following diagnosis and treatment.

Although the present invention has been described with reference to the preferred embodiment thereof, it is apparent to those skilled in the art that a variety of modifications and changes may be made without departing from the scope of the present invention which is intended to be defined by the appended claims.

What is claimed is:

1. A method for positioning an ultrasonic probe on a body surface of a patient using an auxiliary positioning device, said auxiliary positioning device comprising a flexible adjusting member having a first end coupled with a fixing member and a second end coupled with a parallel light source, said parallel light source having a projection hole for passing a parallel light beam emitted from said parallel light source and a cylindrical lens mounted in front of said projection hole for converting said parallel light beam to a fanned light beam, and said method comprising the steps of;

fixing said auxiliary positioning device on said ultrasonic probe with said fixing member;

defining a correction line on said body surface;

marking a surface of said ultrasonic probe with a baseline, said baseline being aligned with a scanning sectional plane of said ultrasonic probe;

aligning and placing said ultrasonic probe on said body surface so that said scanning sectional plane, said base line and said correction line are aligned; and bending and adjusting said flexible adjusting member so that a projection line formed by said fanned light beam is aligned with said base line, said scanning sectional plane and said correction line.

2. The method as claimed in claim 1, wherein said light source is a laser light source.

3. The method as claimed in claim 1, wherein said fixing member is a fixing clamp.

4. The method as claimed in claim 1, wherein said cylindrical lens is a circular cylindrical lens.

5. The method as claimed in claim 1, wherein said cylindrical lens is a biconvex cylindrical lens.

6. The method as claimed in claim 1, wherein said cylindrical lens is a convex-concave cylindrical lens.

7. The method as claimed in claim 1, wherein said cylindrical lens is a plano-convex cylindrical lens.

8. The method as claimed in claim 1, wherein said cylindrical lens is a plano-concave cylindrical lens.

9. The method as claimed in claim 1, wherein said cylindrical lens is a biconcave cylindrical lens.

10. The method as claimed in claim 1, wherein a battery pack is mounted between said fixing member and said flexible adjusting member.

\* \* \* \* \*